(12) United States Patent
Petry et al.

(10) Patent No.: US 7,737,144 B2
(45) Date of Patent: Jun. 15, 2010

(54) PYRIMIDO[5,4-E][1,2,4]TRIAZINE-5-7-DIONES, PROCESSES FOR PREPARING THEM AND THEIR USE

(75) Inventors: Stefan Petry, Frankfurt (DE); Karl-Heinz Baringhaus, Wolfersheim (DE); Norbert Tennagels, Frankfurt (DE); Guenter Mueller, Sulzbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 227 days.

(21) Appl. No.: 11/770,106

(22) Filed: Jun. 28, 2007

(65) Prior Publication Data

US 2008/0032984 A1 Feb. 7, 2008

Related U.S. Application Data

(63) Continuation of application No. 10/760,509, filed on Jan. 20, 2004, now abandoned.

(60) Provisional application No. 60/478,756, filed on Jun. 16, 2003.

(30) Foreign Application Priority Data

Jan. 20, 2003 (DE) .............................. 103 01 788

(51) Int. Cl.
*C07D 487/04* (2006.01)
*A61K 31/53* (2006.01)
*A61P 35/00* (2006.01)
*A61P 31/10* (2006.01)

(52) U.S. Cl. ..................................... 514/243; 544/184
(58) Field of Classification Search ................. 544/184; 514/243
See application file for complete search history.

(56) References Cited

U.S. PATENT DOCUMENTS

| | | | |
|---|---|---|---|
| 5,190,923 | A | 3/1993 | Vincent et al. |
| 6,221,633 | B1 | 4/2001 | Ertl |
| 6,221,897 | B1 | 4/2001 | Frick et al. |
| 6,245,744 | B1 | 6/2001 | Frick et al. |
| 6,376,509 | B1 | 4/2002 | Bakshi et al. |
| 6,380,230 | B1 | 4/2002 | Brodin et al. |
| 6,399,640 | B1 | 6/2002 | Sahoo et al. |
| 6,469,024 | B2 | 10/2002 | Li et al. |
| 6,624,185 | B2 | 9/2003 | Glombik |
| 6,635,653 | B2 | 10/2003 | Goehring et al. |
| 6,908,926 | B1 | 6/2005 | Dorwald et al. |

FOREIGN PATENT DOCUMENTS

| | | |
|---|---|---|
| GB | 2039883 A | 8/1980 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 00/40569 | 7/2000 |
| WO | WO 00/64876 | 11/2000 |
| WO | WO 00/66585 | 11/2000 |
| WO | WO 00/71549 | 11/2000 |
| WO | WO 01/09111 | 2/2001 |
| WO | WO 01/83451 | 11/2001 |
| WO | WO 02/20525 | 3/2002 |

OTHER PUBLICATIONS

Asakawa A. et al., Cocaine-Amphetamine-Regulated Transcript Influences Energy Metabolism, Anxiety and Gastic Emptying in Mice, Hormone and Metabolic Research, (2001) vol. 33, No. 9, pp. 554-558.

Brown et al, Aza Analogs of Pteridine. III. 3-Amino- from 3-alkoxy-pyrimido(5,4-e)-as-triazin-5-ones prepared by cyclization of 3-ethoxy-1,2,4-triazines or other means, Australian Journal of Chemistry, vol. 27(8), 1974; pp. 1781-1790.

Lee Daniel W et al., Leptin agonists as a potential approach to the treatment of obesity, Drugs of the Future, 2001, vol. 26(9), pp. 873-881.

Lioa, T. et. al., Synthesis of 1-Demethyltoxoflavin (8-Demethytfervenulin)1, Journal of Organic Chemistry, vol. 31, (1965) pp. 900-902.

N. K. Tonks et al., Characterization of the Major Protein-tyrosine-phosphatases of Human Placenta, Journal of Biological Chemistry, vol. 263, No. 14, May 15, 1988, pp. 6731-6737.

Okada H. et al., Synthesis and Antitumor Activities of Prodrugs of Benzoylphenylureas, Chem. Pharm. Bull., (1994), vol. 42, No. 1, pp. 57-61.

P. Tyle, Iontophoretic Devices for Drug Delivery, Pharmaceutical Research, vol. 3, No. 6, 1986.

(Continued)

Primary Examiner—Venkataraman Balasubramanian
(74) Attorney, Agent, or Firm—Barbara E. Kurys

(57) ABSTRACT

The invention relates to pyrimido[5,4-e][1,2,4]triazine-5,7-diones, pharmaceutically acceptable salts thereof and physiologically functional derivatives.

The invention therefore relates to compounds of the formula I,

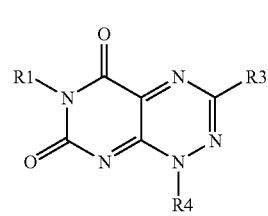

in which the radicals have the given meanings, and to their physiologically tolerated salts and processes for preparing them. The compounds are suitable for use as antidiabetics, for example.

3 Claims, No Drawings

OTHER PUBLICATIONS

P.A. Lanzetta et al., An Improved Assay for Nanomole Amounts of Inorganic Phosphate, Analytical Biochemistry, vol. 100, 1979, pp. 95-97.

Ramachandran et al, Protein Tyrosine Phosphatase 1B: A Novel Target for Type 2 Diabetes and Obesity, Curr. Top. Med. Chem., vol. 3(7), 1003; pp. 749-757.

Salvador Javier et al., Perspectives in the therapeutic use of leptin, Expert Opinion on Pharmacotherapy 2001, 2(10), 1615-1622.

T. R. Burke et al., Small Molecule Interactions with Protein-Tyrosine Phosphatase PTP1B and Their Use in Inhibitor Design, Biochemistry, vol. 35, 1996, pp. 15989-15996.

Temple et al, Pyrimido[5,4-e]-as-Triazines. III. The Preparation and some Reactions of 5-Subsitituted Pyrimido[5,4-e]-as-Triazines, J. Org. Chem., vol. 34(7), 1969. pp. 2102-2106.

W. Cromlish et al., Selective Inhibition of Cyclooxygenase-1 and -2 Using Intact Insect Cell Assays, Biochemical Pharmacology, vol. 52, 1996, pp. 1777-1785.

Yoneda et al, Convenient Synthesis of Toxoflavins, Toxoflavin 4-oxides, and 1-demethyltoxoflavins, Chemical & Pharmaceutical Bulletin, vol. 23(9), 1975, pp. 2001-2009.

Yoneda, F. et. al. , Antitumor Agent, Patent Abstracts of Japan vol. Jan. 30, 1998.

Yoneda,F. et. al., A Convenient Synthesis of Toxoflavins. Toxoflavin 4-Oxides and 1-Demethylloxoflavins, Chemical and Pharmaceutical Bulletin vol. 23, No. 9 (1975) pp. 2001-2009.

Zunft, H. et al., Carob Pulp Preparation for Treatment of Hypercholesterolemia, Advances in Therapy, 2001, vol. 18(5), pp. 230-236.

PYRIMIDO[5,4-E][1,2,4]TRIAZINE-5-7-DIONES, PROCESSES FOR PREPARING THEM AND THEIR USE

The present invention relates to pyrimido[5,4-e][1,2,4]triazine-5,7-diones and to their physiologically tolerated salts and physiologically functional derivatives.

JP 96-67814 describes compounds of a similar structure as being antineoplastic agents.

The object of the invention was to provide compounds which can be used to prevent and treat diabetes type 1 and type 2. In addition, the compounds should bring about a perceptible reduction in blood sugar level.

The invention therefore relates to compounds of the formula I,

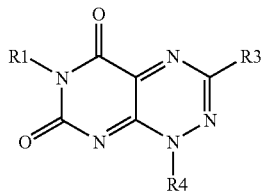

I wherein
R1, R3 and R4 are each independently H, F, Cl, Br, OH, $CF_3$, $NO_2$, CN, $OCF_3$, $(C_1\text{-}C_6)$-alkyl, $(C_2\text{-}C_6)$-alkenyl, $(C_2\text{-}C_6)$-alkynyl, $O\text{—}(C_1\text{-}C_{10})$-alkyl, $O\text{—}(C_1\text{-}C_{10})$-alkenyl, $O\text{—}(C_2\text{-}C_{10})$-alkynyl, $S\text{—}(C_1\text{-}C_6)$-alkyl, $S\text{—}(C_2\text{-}C_6)$-alkenyl, $S\text{—}(C_2\text{-}C_6)$-alkynyl, $(C_3\text{-}C_7)$-cycloalkyl, $(C_3\text{-}C_7)$-cycloalkyl-$(C_1\text{-}C_4)$-alkyl,
wherein said $(C_1\text{-}C_6)$-alkyl, $(C_2\text{-}C_6)$-alkenyl, $(C_2\text{-}C_6)$-alkynyl, $O\text{—}(C_1\text{-}C_{10})$-alkyl, $O\text{—}(C_1\text{-}C_{10})$-alkenyl, $O\text{—}(C_2\text{-}C_{10})$-alkynyl, $S\text{—}(C_1\text{-}C_6)$-alkyl, $S\text{—}(C_2\text{-}C_6)$-alkenyl, $S\text{—}(C_2\text{-}C_6)$-alkynyl, $(C_3\text{-}C_7)$-cycloalkyl and $(C_3\text{-}C_7)$-cycloalkyl-$(C_1\text{-}_4)$-alkyl radicals are optionally substituted with one or more groups independently selected from F, Cl, Br, SO-phenyl, $SO_2$-phenyl or phenyl,
wherein said SO-phenyl, $SO_2$-phenyl or phenyl radicals is optionally substituted with F, Cl, Br, R13 or OR13, COOR13, CON(R14)(R15), N(R14)(R15), CO-heteroalkyl, $O\text{—}SO\text{—}(C_1\text{-}C_6)$-alkyl, $O\text{—}SO_2\text{-}(C_1\text{-}C_6)$-alkyl, $O\text{—}SO_2\text{—}(C_6\text{-}C_{10})$-aryl, $O\text{—}(C_6\text{-}C_{10})$-aryl,
wherein said $O\text{—}SO_2\text{—}(C_6\text{-}C_{10})$-aryl and $O\text{—}(C_6\text{-}C_{10})$-aryl radicals is optionally mono- or disubstituted with F, Cl, CN, OR13, R13, $CF_3$ or $OCF_3$,
$SO\text{—}(C_1\text{-}C_6)$-alkyl, $SO_2\text{—}(C_1\text{-}C_6)$-alkyl, $SO_2\text{—}(C_6\text{-}C_{10})$-aryl,
wherein said $SO_2\text{—}(C_6\text{-}C_{10})$-aryl radical is optionally mono- or disubstituted with F, Cl, Br, CN, OR13, R13, $CF_3$, $OCF_3$, COOR13 or CON(R14)(R15), $SO_2\text{—}N(R14)(R15)$ or heteroalkyl;
R13, R14 and R15 are, independently of each other, H, $(C_1\text{-}C_6)$-alkyl or phenyl;

and physiologically acceptable salts thereof.

Very particular preference is given to compounds of the formula I in which one or more radical(s) has/have the following meaning:
R1 is $(C_1\text{-}C_6)$-alkyl;
R3 is $(C_1\text{-}C_6)$-alkyl-phenyl or $(C_2\text{-}C_6)$-alkenyl-phenyl, wherein the phenyl ring of said $(C_1\text{-}C_6)$-alkyl-phenyl and $(C_2\text{-}C_6)$-alkenyl-phenyl groups is optionally substituted by F, Cl, Br, OR13 or R13;
R4 is $(C_1\text{-}C_6)$-alkyl or $(C_1\text{-}C_6)$-alkylene-D;
R13 is $(C_1\text{-}C_6)$-alkyl or phenyl;

and the physiologically tolerated salts thereof.

The alkyl radicals in the substituents R1, R3 and R4 can be either straight-chain or branched.

If radicals or substituents, such as COOR13, can occur more than once in the compounds of the formula I, they can then all, independently of each other, have the given meanings and be identical or different.

Because they are more soluble in water than the starting compounds or basis compounds, pharmaceutically tolerated salts are particularly suitable for medical applications. These salts must possess a pharmaceutically tolerated anion or cation. Suitable pharmaceutically tolerated acid addition salts of the compounds according to the invention are salts of inorganic acids, such as hydrochloric acid, hydrobromic acid, phosphoric acid, metaphosphoric acid, nitric acid and sulfuric acid, and also of organic acids, such as acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically tolerated basic salts are ammonium salts, alkali metal salts (such as sodium salts and potassium salts), alkaline earth metal salts (such as magnesium salts and calcium salts), trometamol (2-amino-2-hydroxymethyl-1,3-propanediol), diethanolamine, lysine or ethylene-diamine.

Salts containing an anion which is not pharmaceutically tolerated, such as trifluoroacetate, also belong within the scope of the invention as useful intermediates for preparing or purifying pharmaceutically tolerated salts and/or for use in nontherapeutic applications, for example in-vitro applications.

The term "physiologically functional derivative", which is used here, denotes any physiologically tolerated derivative of a compound of the formula I according to the invention, e.g. an ester which is able, on being administered to a mammal, such as a human, to form (directly or indirectly) a compound of the formula I or an active metabolite thereof.

The physiologically functional derivatives also include prodrugs of the compounds according to the invention, as described, for example, in H. Okada et al., Chem. Pharm. Bull. 1994, 42, 57-61. Such prodrugs can be metabolized in vivo to give a compound according to the invention. These prodrugs may or may not themselves be active.

The compounds according to the invention can also be present in different polymorphic forms, for example as amorphous and crystalline polymorphic forms. All the polymorphic forms of the compounds according to the invention belong within the scope of the invention and are another aspect of the invention.

In that which follows, all references to "compound(s) according to formula I" relate to (a) compound(s) of the formula I as described above and to its (their) salts, solvates and physiologically functional derivatives as described herein.

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The compound(s) of the formula (I) can also be administered in combination with (an) other active compound(s).

The quantity of a compound according to formula I which is required in order to achieve the desired biological effect depends on a number of factors, e.g. the specific compound which is selected, the intended use, the type of administration and the clinical state of the patient. In general, the daily dose lies in a range from 0.3 mg to 100 mg (typically from 3 mg to 50 mg) per day per kilogram of body weight, e.g. 3-10 mg/kg/day. An intravenous dose can, for example, lie in the range from 0.3 mg to 1.0 mg/kg, with it being possible for this dose to be expediently administered as an infusion of from 10 ng to 100 ng per kilogram per minute. Infusion solutions which are suitable for these purposes can contain, for example, from 0.1 ng to 10 mg, typically from 1 ng to 10 mg per milliliter. Single doses can contain, for example, from 1 mg to 10 g of the active compound. Consequently, ampoules for injections can contain, for example, from 1 mg to 100 mg, while single dose formulations which can be administered orally, such as tablets or capsules, can, for example, contain from 1.0 to 1000 mg, typically from 10 to 600 mg. While the compounds according to formula I can themselves be used as the compound for treating the abovementioned conditions, they are preferably present, together with a tolerated excipient, in the form of a pharmaceutical composition. The excipient naturally has to be tolerated, in the sense that it is compatible with the other constituents of the composition and is not harmful to the health of the patient. The excipient can be a solid or a liquid or both and is preferably formulated with the compound as a single dose, for example as a tablet which can contain from 0.05% to 95% by weight of the active compound. Other pharmaceutically active substances can also be present, including other compounds according to formula I. The pharmaceutical compositions according to the invention can be prepared using one of the known pharmaceutical methods, which essentially consist in mixing the constituents with pharmacologically tolerated carrier substances and/or auxiliary substances.

Pharmaceutical compositions according to the invention are those which are suitable for oral, rectal, topical, peroral (e.g. sublingual) or parenteral (e.g. subcutaneous, intramuscular, intradermal or intravenous) administration even if the most suitable mode of administration depends, in each individual case, on the nature and severity of the condition to be treated and on the nature of the compound according to formula I which is in each case employed. Sugar-coated formulations and sugar-coated delayed-release formulations also belong within the scope of the invention.

Formulations which are acid-resistant and gastric juice-resistant are preferred. Suitable gastric juice-resistant coatings include cellulose acetate phthalate, polyvinyl acetate phthalate, hydroxypropylmethyl cellulose phthalate and anionic polymers of methacrylic acid and methyl methacrylate.

Suitable pharmaceutical compounds for oral administration can be present in separate units, such as capsules, cachets, sucking tablets or tablets which in each case contain a specific quantity of the compound according to formula I; as powders or granulates; as a solution or suspension in an aqueous or non-aqueous liquid; or as an oil-in-water or a water-in-oil emulsion. As has already been mentioned, these compositions can be prepared using any suitable pharmaceutical method which includes a step in which the active compound and the excipient (which can consist of one or more additional constituents) are brought into contact. In general, the compositions are prepared by uniformly and homogeneously mixing the active compound with a liquid and/or finely divided solid excipient, after which the product is molded, if necessary. Thus, a tablet can be prepared, for example, by means of a powder or granulate of the compound being pressed or molded, where appropriate together with one or more additional constituents. Pressed tablets can be prepared by tableting the compound in freely flowing form, such as a powder or granulate, which is mixed, where appropriate, with a binder, lubricant, inert diluent and/or a (several) surface-active/dispersing agent(s) in a suitable machine. Molded tablets can be prepared by molding the pulverulent compound, which is moistened with an inert, liquid diluent, in a suitable machine.

Pharmaceutical compositions which are suitable for peroral (sublingual) administration include sucking tablets which contain a compound according to formula I together with a flavoring agent, usually sucrose and gum arabic or tragacanth, and lozenges, which include the compound in an inert base such as gelatin and glycerol or sucrose and gum arabic.

Suitable pharmaceutical compositions for parenteral administration preferably include sterile, aqueous preparations of a compound according to formula I which are preferably isotonic with the blood of the intended recipient. These preparations are preferably administered intravenously even if the administration can also take place subcutaneously, intramuscularly or intradermally as an injection. These preparations can preferably be prepared by mixing the compound with water and making the resulting solution sterile and isotonic with the blood. In general, injectable compositions according to the invention contain from 0.1 to 5% by weight of the active compound.

Suitable pharmaceutical compositions for rectal administration are preferably present as single-dose suppositories. These can be prepared by mixing a compound according to formula I with one or more conventional solid excipients, for example cocoa butter, and molding the resulting mixture.

Suitable pharmaceutical compositions for topical application on the skin are preferably present as an ointment, cream, lotion, paste, spray, aerosol or oil. Vaseline, lanolin, polyethylene glycols, alcohols, and combinations of two or more of these substances can be used as the excipient. In general, the active compound is present at a concentration of from 0.1 to 15% by weight of the composition, for example of from 0.5 to 2%.

Transdermal administration is also possible. Suitable pharmaceutical compositions for transdermal applications can be present as individual plasters which are suitable for long-term, close contact with the epidermis of the patient. Such plasters expediently contain the active compound in an optionally buffered, aqueous solution, dissolved and/or dispersed in an adhesive or dispersed in a polymer. A suitable active compound concentration is from approx. 1% to 35%, preferably from approx. 3% to 15%. As a special option, the active compound can, as described, for example, in Pharmaceutical Research, 2(6): 318 (1986), be released by means of electrotransport or iontophoresis.

The following are suitable to use as additional active compounds for the combination preparations: all the antidiabetics which are named in chapter 12 in the Roten Liste [Red List] 2001. They can be combined with compounds of the formula I according to the invention, particularly for the purpose of synergistically improving the effect. The active compound combination can be administered either by separately administering the active compounds to the patient or administering them in the form of combination preparations in which several active compounds are present in one pharmaceutical preparation. Most of the active compounds which are cited below are disclosed in USP Dictionary of USAN and International Drug Names, US Pharmacopoeia, Rockville 2001.

Antidiabetics include insulin and insulin derivatives, such as Lantus® (see www.lantus.com) or HMR 1964, rapidly acting insulins (see U.S. Pat. No. 6,221,633), GLP-1 derivatives, such as those which Novo Nordisk A/S has disclosed in WO 98/08871, and also orally active hypoglycaemic active compounds.

The orally active hypoglycaemic active compounds preferably include sulfonylureas, biguanidines, meglitinides, oxadiazolidinediones, thiazolidinediones, glucosidase inhibitors, glucagon antagonists, GLP-1-agonists, potassium channel openers, such as those which Novo Nordisk A/S has disclosed in WO 97/26265 and WO 99/03861, insulin sensitizers, inhibitors of liver enzymes which are involved in stimulating gluconeo-genesis and/or glycogenolysis, modulators of glucose uptake, compounds which alter fat metabolism, such as antihyperlipidaemic active compounds and antilipidaemic active compounds, compounds which decrease food intake, PPAR agonists and PXR agonists, and active compounds which act on the ATP-dependent potassium channel in the beta cells.

In one embodiment of the invention, the compounds of formula I are administered in combination with an HMGCoA reductase inhibitor, such as simvastatin, fluvastatin, pravastatin, lovastatin, atorvastatin, cerivastatin or rosuvastatin.

In another embodiment of the invention, the compounds of formula I are administered in combination with a cholesterol absorption inhibitor, such as Ezetimibe, Tiqueside or Pamaqueside.

In another embodiment of the invention, the compounds of the formula I are administered in combination with a PPAR gamma agonist, such as rosiglitazone, pioglitazone, JTT-501 or GI 262570.

In another embodiment of the invention, the compounds of formula I are administered in combination with a PPAR alpha agonist, such as GW 9578 or GW 7647.

In another embodiment of the invention, the compounds of the formula I are administered in combination with a mixed PPAR alpha/gamma agonist, such as GW 1536, AVE 8042, AVE 8134 or AVE 0847, or as described in PCT/US00/11833, PCT/US00/11490 or DE10142734.4.

In another embodiment of the invention, the compounds of formula I are administered in combination with a fibrate, such as Fenofibrate, Clofibrate or Bezafibrate.

In another embodiment of the invention, the compounds of the formula I are administered in combination with an MTP inhibitor, such as Implitapide, BMS-201038 or R-103757.

In another embodiment of the invention, the compounds of formula I are administered in combination with a bile acid absorption inhibitor (see, e.g., U.S. Pat. Nos. 6,245,744 or 6,221,897), such as HMR 1741.

In another embodiment of the invention, the compounds of the formula I are administered in combination with a CETP inhibitor, such as JTT-705.

In another embodiment of the invention, the compounds of formula I are administered in combination with a polymeric bile acid adsorber, such as Cholestyramine or Colesevelam.

In another embodiment of the invention, the compounds of formula I are administered in combination with an LDL receptor inducer (see U.S. Pat. No. 6,342,512), such as HMR1171 or HMR 1586.

In another embodiment of the invention, the compounds of the formula I are administered in combination with an ACAT inhibitor, such as Avasimibe.

In another embodiment of the invention, the compounds of the formula I are administered in combination with an antioxidant, such as OPC-14117.

In another embodiment of the invention, the compounds of the formula I are administered in combination with a lipoprotein lipase inhibitor, such as NO-1886.

In another embodiment of the invention, the compounds of the formula I are administered in combination with an ATP citrate lyase inhibitor, such as SB-204990.

In another embodiment of the invention, the compounds of the formula I are administered in combination with a squalene synthetase inhibitor, such as BMS-188494.

In another embodiment of the invention, the compounds of the formula I are administered in combination with a lipoprotein(a) antagonist, such as CI-1027 or nicotinic acid.

In another embodiment of the invention, the compounds of the formula I are administered in combination with a lipase inhibitor, such as Orlistat.

In another embodiment of the invention, the compounds of the formula I are administered in combination with insulin.

In another embodiment, the compounds of the formula I are administered in combination with a sulfonylurea, such as Tolbutamide, Glibenclamide, Glipizide or Glimepiride.

In another embodiment, the compounds of the formula I are administered in combination with a biguanide, such as Metformin.

In yet another embodiment, the compounds of formula I are administered in combination with a Meglitinide, such as Repaglinide.

In another embodiment, the compounds of formula I are administered in combination with a thiazolilinedione, such as Troglitazone, Ciglitazone. Pioglitazone, Rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In another embodiment, the compounds of the formula I are administered in combination with an α-glucosidase inhibitor, such as Miglitol or Acarbose.

In another embodiment, the compounds of the formula I are administered in combination with an active compound which acts on the ATP-dependent potassium channel in beta cells, such as Tolbutamide, Glibenclamide, Glipizide, Glimepiride or Repaglinide.

In another embodiment, the compounds of formula I are administered in combination with more than one of the abovementioned compounds, e.g. in combination with a sulfonylurea and Metformin, a sulfonylurea and Acarbose, Repaglinide and Metformin, insulin and a sulfonylurea, insulin and Metformin, insulin and Troglitazone, insulin and Lovastatin, etc.

In another embodiment, the compounds of the formula I are administered in combination with CART modulators (see "cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid-{4-[(4-aminoquinazolin-2-ylamino)methyl] cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), Orexin antagonists (e.g. 1-(2-methylbenzoxazol-6-yl)-3-[1,5]naphthyridin-4-yl urea hydrochloride (SB-334867-A)), H3 agonists (3-cyclohexyl-1-(4,4-dimethyl-1,4,6,7-tetrahydroimidazo[4,5-c]pyridin-5-yl)-propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. Urocortin), Urocortin agonists, β3-agonists (e.g. 1-(4-chloro-3-methanesulfonyl-methylphenyl)-2-[2-(2,3-dimethyl-1H-indol-6-yloxy)ethylamino]ethanol hydrochloride (WO 01/83451)), MSH (melanocyte-stimulating hormone) agonists, CCK-A agonists (e.g. {2-[4-(4-chlor-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. Dexfenfluramine), mixed serotoninergic and noradrenergic compounds (e.g. WO 00/71549), 5HT agonists, e.g. 1-(3-ethylbenzofuran-7-yl) piperazine oxalic acid salt (WO 01/09111), Bombesin agonists, Galanin antagonists, growth hormone (e.g. human growth hormone), growth hormone-releasing compounds (tert-butyl 6-benzyloxy-1-(2-diisopropylaminoethylcarbamoyl)-3,4-dihydro-1H-isoquinoline-2-carboxylate (WO 01/85695)), TRH agonists (see, e.g. EP 0 462 884) uncoupling protein 2 or protein 3 modulators, leptin agonists (see, e.g. Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (Bromocriptine, Doprexin), lipase/amylase inhibitors (e.g. WO 00/40569), PPAR modulators (e.g. WO 00/78312), RXR modulators or TR-β-agonists.

In another embodiment of the invention, the other active compound is leptin; see, e.g., "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment, the other active compound is Dexamphetamine or amphetamine.

In another embodiment, the other active compound is Fenfluramine or Dexfenfluramine.

In yet another embodiment, the other active compound is Sibutramine.

In another embodiment, the other active compound is Orlistat.

In another embodiment, the other active compound is Mazindol or Phentermine.

In another embodiment, the compounds of the formula I are administered in combination with ballast substances, preferably insoluble ballast substances (see, e.g., carob/Caromax®) (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hoechst, 65926 Frankfurt/ Main)). The combination with Caromax® can be effected in one preparation or by means of separating administering compounds of the formula I and Caromax®. In this connection, Caromax® can also be administered in the form of foodstuffs, for example in bread, cakes and pastries or muesli bars.

It will be understood that each suitable combination of the compounds according to the invention with one or more of the abovementioned compounds and, if desired, one or more additional pharmacologically active substances, is regarded as coming within the protected scope of the present invention.

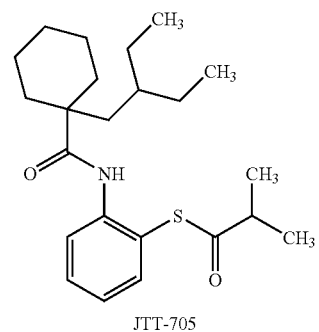

JTT-705

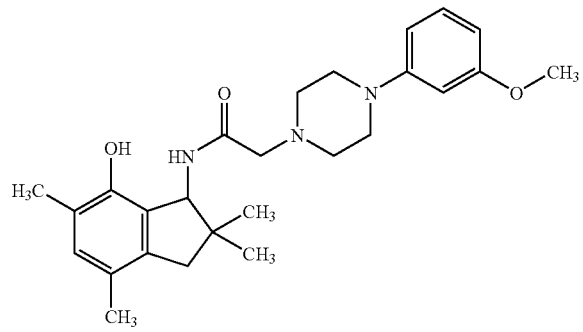

OPC-14117

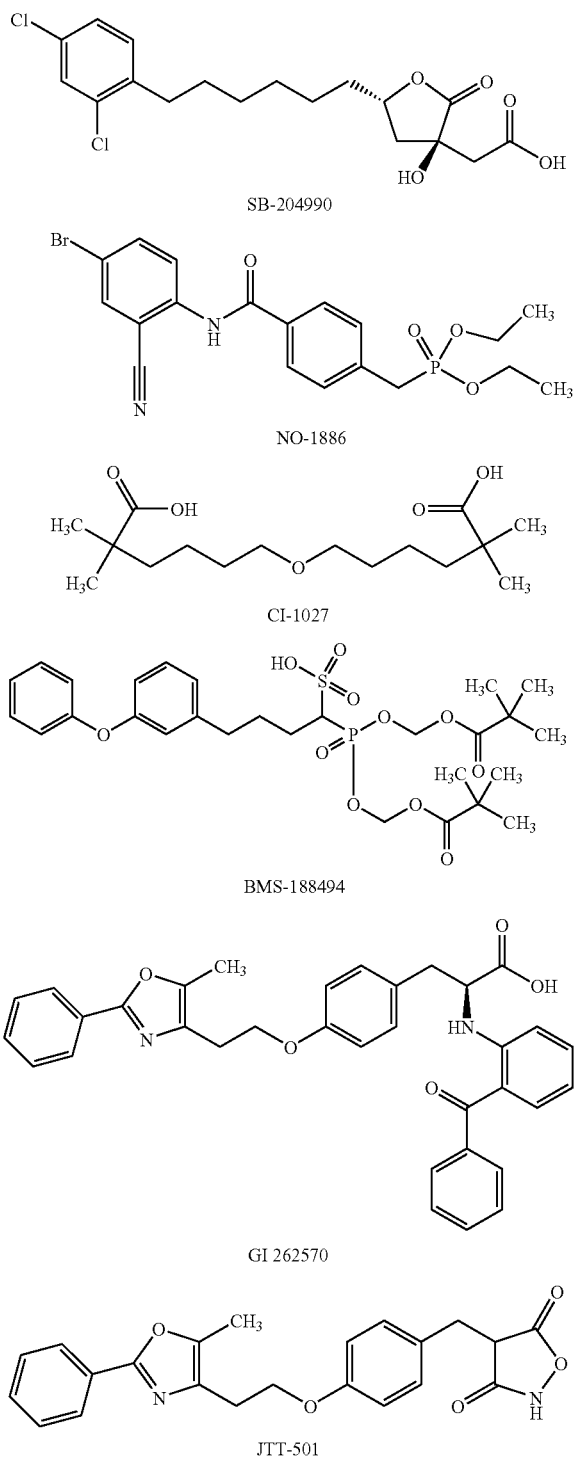

TABLE 1

Examples of Formula I

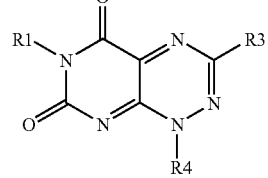

| Bsp. | R1 | R3 | R4 | MS* |
|---|---|---|---|---|
| 1 | $CH_3$ | 4-methylphenylethyl-$CH_3$ | $CH_2$—$CH_3$ | ok |
| 2 | $CH_3$ | phenyl | $CH_2$—$CH_3$ | ok |
| 3 | $CH_3$ | phenyl | $CH_2$—$CH_3$ | ok |
| 4 | $CH_3$ | styryl | $(CH_2)_2$—D | ok |
| 5 | $CH_3$ | 3-(phenoxy)-methylphenyl | $(CH_2)_3$—$CH_3$ | ok |
| 6 | $CH_3$ | 3-(phenoxy)-methylphenyl | $CH_2$—$CH_3$ | ok |
| 7 | $CH_3$ | 3-(phenoxy)-methylphenyl | $CH_2$—$CH_3$ | ok |
| 8 | $CH_3$ | 3,4-dimethoxy-methylphenyl | $(CH_2)_3$—$CH_3$ | ok |

*The statement "MS is ok" is understood as meaning that a mass spectrum or HPLC/MS was measured and the molar peak (molar mass + H⁺) was detected in it.

The citation of any reference herein should not be construed as an admission that such reference is available as "Prior Art" to the instant application.

Various publications are cited herein, the disclosures of which are incorporated by reference in their entireties.

The examples which are produced below serve to explain the invention without, however, restricting it.

The compounds of the formula I, and/or their physiologically tolerated salts and/or their prodrugs can be used for producing pharmaceuticals.

These pharmaceuticals are suitable, in particular for treating diabetes type I and type 2, insulin resistance and pathological obesity. In addition to this, they are also suitable for treating excessively high blood fat values, high blood pressure, atherosclerosis, malfunctions of the immune system, autoimmune diseases, allergic diseases such as asthma, in connection with osteoporosis, proliferation disturbances such as cancer and psoriasis, diseases involving a reduced or increased production of growth factors, hormones or cytokines which induce the release of growth hormones, infectious diseases or diseases of the nervous system, such as Alzheimer's and schizophrenia.

In addition, the compounds of the formula I, and/or their physiologically tolerated salts and/or their prodrugs can be used for producing a pharmaceutical, with this pharmaceutical inhibiting a PTPase. In this connection PTP1B, CD45, LAR, SHP-1, SHP-2, PTPa or HePTP can, in particular, occur as PTPases.

Finally, compounds of formula I, and/or their physiologically tolerated salts and/or their prodrugs can be used for producing a pharmaceutical, with it being possible to employ this pharmaceutical for treating diseases, in particular diabetes type I and type 2, insulin resistance, pathological obesity, excessively high blood fat values, high blood pressure, athero-sclerosis, malfunctions of the immune system, autoimmune diseases, allergic diseases such as asthma, in connection with osteoporosis, proliferation disturbances such as cancer and psoriasis, diseases involving a reduced or increased production of growth factors, hormones or cytokines which induce release of growth hormones, diseases of the nervous system such as Alzheimer's and schizophrenia and infectious diseases.

In addition, compounds of the formula I, and/or their physiologically tolerated salts and/or their prodrugs can be employed for producing a pharmaceutical for treating late damage in diabetes (such as nephropathy, retinopathy and neuropathy), and also cardiac infarction, myocardial infarction, peripheral arterial occlusion diseases, thromboses, arterio-sclerosis, syndrome X, obesity, insulin resistance, inflammations, immune diseases, autoimmune diseases, such as AIDS, asthma, osteoporosis, cancer, psoriasis, Alzheimer's, schizophrenia and infectious diseases.

The invention relates to the production of a pharmaceutical which comprises at least one compound of this invention, with the active compound being mixed with a pharmaceutically suitable excipient and this mixture being brought into a form which is suitable for administration.

The activity of the compounds was tested as follows:

Inhibiting Phosphotyrosine Phosphatase 1B (PTP1B)

The setting up and implementation of an in-vitro assay for detecting a phosphatase-inhibiting effect of the compounds according to the invention are described below. The isolation of the enzyme preparation and the implementation of the assay are described.

Isolating the Enzyme Preparation:

A) Cell Culture:

Sf9 (invitrogen) cells are cultured in spinner flasks at 28° C. in Grace's supplement medium (Gibco-BRL) containing 10% heat-inactivated foetal calf serum (Gibco-BRL) following the protocol of Summers and Smith (A Manual for Methods for Baculovirus Vectors and Insect Culture Procedures [Bulletin No. 15555]. Texas A & M University, Texas Agricultural Experiment Station, College Station, Tex., 1987).

Constructing recombinant baculovirus transfer vectors: cDNA encoding the regulatory and catalytic domains of human PTP1B, but without the carboxy terminal hydrophobic region (corresponding to 1-299 aa), was obtained by means of the polymerase chain reaction, using primers containing favorable cloning sites and suitable cDNA templates, and then cloned into baculovirus expression vectors (Amersham Pharmacia Biotech.). The recombinant baculoviruses were prepared using the Bac-to-Bac baculovirus expression system (Gibco-BRL). In brief, the gene was cloned into the pFASTBAC donor plasmid, which possesses a FLAG sequence at the 5' end of the cDNA. The resulting plasmid was transformed into competent DH10BAC *Escherichia coli* cells. Following transposition and antibiotic selection, the recombinant plasmid DNA was isolated from selected *E. coli* colonies and then used for transfecting Sf9 insect cells. The virus particle in the supernatant medium was amplified three times up to a viral stock volume of 500 ml.

B) Producing Recombinant Protein:

The infection of a 500 ml spinner culture of Sf9 cells with baculovirus was essentially carried out as described by Summers and Smith (see above). Sf9 cells, at a density of $1-3 \times 10^6$ cells/ml, were pelleted by centrifuging at 300 g for 5 min, after which the supernatant was removed and the cells were resuspended, at a density of $1 \times 10^7$ cells/ml, in a suitable recombinant viral stock (MOI 10). After gently shaking at room temperature for 1.5 hrs, fresh medium was added in order to achieve a cell density of $1 \times 10^6$ cells/ml. The cells were then cultured in suspension at 28° C. for suitable periods post infection.

C) Cellular Fractionation and Total Cell Extracts from Infected Sf9 Cells:

A suitable time after the post infection, aliquots were subjected to an analysis of protein expression using SDS—PAGE and Western blot analysis. The cellular fractionation was carried out as described (Cromlish, W. and Kennedy, B. Biochem. Pharmacol. 52: 1777-1785, 1996). Total cell extracts were obtained from 1 ml aliquots of the infected Sf9 cells after specified times post infection. The pelleted cells (300 g, 5 min) were washed once in phosphate-buffered saline (4° C.), resuspended in 50 µl of water and disrupted by being repeatedly frozen and thawed. Protein concentrations were determined using the Bradford method (Pierce) and bovine serum albumin as standard.

Implementing the Assay:

A) Dephosphorylating a Phosphopeptide:

This assay is based on releasing phosphate from a consensus substrate peptide which is detected in the nanomolar concentration range using the malachite green/ammonium molybdate method (Lanzetta, P. A., Alvarez, L. J., Reinach, P. S., Candia, O. A. Anal Biochem. 100: 95-97, 1979) as adapted for the microtiter plate format. The dodecatrisphosphopeptide, TRDIYETDYYRK (Biotrend, Cologne), corresponds to amino acids 1142-1153 of the catalytic domain of the insulin receptor and is (auto)-phosphorylated at tyrosine residues 1146, 1150 and 1151. The recombinant hPTP1B was diluted with assay buffer (40 mM tris/HCl, pH 7.4, 1 mM EDTA, 20 mM DTT), in accordance with an activity of 1000-1500 nmol/min/mg of protein, and (a 20 µl portion) was then pre-incubated (15 min, 30° C.) in the absence or presence of the test substance (5 µl) at the desired concentration (final conc. DMSO 2% max.) in a total volume of 90 µl (assay buffer). In order to start the dephosphorylation reaction, the peptide substrate (10 µl, prewarmed at 30° C.) was added to the preincubated enzyme preparation with or without test substance (final conc. 0.2-200 µM) and the incubation was continued for 1 hr. The reaction was terminated by adding 100 µl of malachite green hydrochloride (0.45%, 3 parts), ammonium molybdate tetrahydrate (4.2% in 4 N HCl, 1 part) and 0.5% Tween 20 as the stop solution. After incubating at 22° C. for 30 min, in order to develop the color, the absorption at 650 nm was determined using a microtiter plate reader (Molecular Devices). Samples and blanks were measured in triplicate. The PTP1B activity was calculated as nanomoles of phosphate released per min and mg of protein using potassium phosphate as the standard. The inhibition of the recombinant hPTP1B by test substances was calculated as percentages of the phosphatase control. Using a four-parameter non-linear logistic regression curve, the $IC_{50}$ values show significant agreement.

B) Cleaving p-nitrophenyl Phosphate:

This assay is based on the change in the absorption of the non-physiological substrate p-nitrophenylphosphate while it is being cleaved, under standard conditions, to give nitrophenol (Tonks, N. K., Diltz, C. D.; Fischer, E. H. J. Biol. Chem. 263: 6731-6737, 1988; Burke T. R., Ye, B., Yan, X. J. Wang, S. M., Jia, Z. C., Chen, L., Zhang, Z. Y., Barford, D. Biochemistry 35: 15989-15996, 1996). The inhibitors are pipetted, at suitable dilutions, into the reaction mixtures, which contain 0.5-5 mM p-nitrophenyl phosphate. The following buffers are used (total volume, 100 µl): (a) 100 mM sodium acetate (pH 5.5), 50 mM NaCl, 0.1% (w/v) bovine serum albumin, 5 mM glutathione, 5 mM DTT, 0.4 mM EGTA and 1 mM EDTA; (b) 50 mM Hepes/KOH (pH 7.4), 100 mM NaCl, 0.1% (w/v) bovine serum albumin, 5 mM glutathione, 5 mM DTT and 1 mM EDTA. The reaction was started by adding enzyme and was carried out, at 25° C. for 1 hr. in microtiter plates. The reaction was terminated by adding 100 µl of 0.2 N NaOH. The enzyme activity was determined by measuring the absorption at 405 nm using suitable corrections for the absorption of the test substances of p-nitrophenyl phosphate. The results were expressed as percentages of the control, with the quantity of p-nitrophenol formed in the test substance-treated samples (nmol/min/mg protein) being compared with the quantity in the untreated samples. The mean value and the standard deviation were calculated, with the IC50 values being determined by regression analysis of the linear portion of the inhibition curves.

C) Cleaving DIFMUP:

This assay is based on the change in the absorption of the non-physiological substrate 6,8-difluoro-4-methylumbelliferyl phosphate (DFMUP) while it is being cleaved to give 6,8-difluoro-4-methylumbelliferyl (internal no. DEAV2002/0001 DE NP). The reaction takes place in a black microtiter plate at a temperature of 37° C. 120 µl of reaction buffer are prepared, with this buffer containing the following components: 100 ng of recombinant human protein tyrosine phosphatase PTP1b/ml; 50 mM Hepes, pH 6.9; 150 mM NaCl; 1 mM EDTA; 2 mM DTT and inhibitors at suitable dilutions. The phosphatase reaction is started by adding 15 µl of DIFMUP solution, which contains the substrate at ten times the desired final concentration in the final volume, and the fluorescence is measured, at time intervals of 30 seconds over 15 minutes, at 358-455 nm in a fluorescence microtiter plate photometer. The measure of the enzyme activity is the increase in fluorescence, which can be represented graphically. The enzymatic activity is reduced in dependence on the inhibitor concentration employed; the inhibitor concentration at which half-maximal enzyme activity is observed is designated the IC50.

TABLE 2

| | Biological activity |
|---|---|
| Ex. | IC50 µM |
| 1 | 0.75 |
| 2 | 0.38 |
| 3 | 0.24 |
| 4 | 0.22 |
| 5 | 5.2 |
| 6 | 0.44 |
| 7 | 0.7 |
| 8 | 2.5 |

It can be seen from the table that the compounds of the formula I inhibit the activity of phosphotyrosine 1B. They are therefore well suited for lowering the blood sugar level and insulin level and for preventing and treating diabetes type 1 and type 2.

The preparation of some examples is described in detail below: the remaining compounds of the formula I were obtained in an analogous manner:

Experimental Section:

Chlorouracil (1)

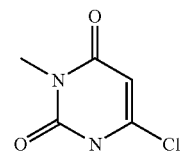

Phosphoryl chloride (55 ml) is carefully added to barbituric acid (10 g, 78.1 mmol) at 0° C. Water (1.7 ml) is then added dropwise such that the temperature does not exceed 5° C. The mixture is boiled under reflux for 5 h and, after it has cooled down, poured onto ice. The product is extracted with ethyl acetate (3×100 ml) and dried ($Na^2 SO_4$). The mixture is filtered and the solvent is distilled off in vacuo.

Yield: 10.7 g (93%)

NMR: H730335

MS: E32934

Ethylhydrazine (2)

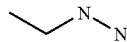

A solution of ethyl bromide (38 ml) in ethanol (50 ml) is added dropwise, while stirring intensively, to hydrazine hydrate (250 ml) such that the temperature does not exceed 30° C. After the addition has come to an end, the mixture is stirred for a further 2 h. Barium oxide is added to the mixture and the product is distilled through a Vigreux column.

Yield: 37 ml.

6-(N-Ethylhydrazino)-3-methyl-1H-pyrimidine-2,4-dione (3)

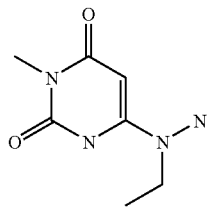

Ethylhydrazine (2 ml) is added to compound I (1.5 g, 8 mmol) and the mixture is stirred at 60° C. After 3.5 h, it was no longer possible to detect any starting material by thin layer chromatography. The mixture is concentrated in vacuo and the product is purified by preparative HPLC.

Yield: 582 mg

EXAMPLES 1 AND 2

1-Ethyl-6-methyl-3-phenyl-1H-pyrimido[5,4-e]1,2,4]triazine-5,7-dione (4) and 1-ethyl-6-methyl4-oxy-3-phenyl-1H-pyrimido[5,4-e][1,2,4]triazine-5,7-dione (5)

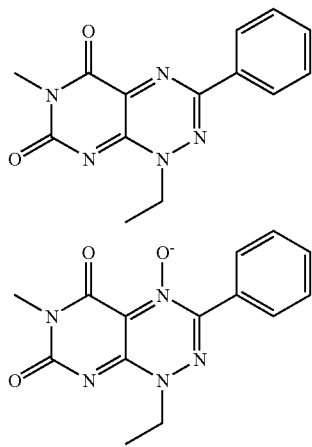

Benzaldehyde (55 µl, 0.54 mmol) is added to a solution of compound 3 (115 mg, 0.54 mmol) in glacial acetic acid (2 ml) and the mixture is stirred at 10° C. for 20 min. An aqueous solution of sodium nitrite (40 mg of NaNO2 in 100 µl of water) is then added and the mixture is stirred at 10° C. for a further 30 min. The mixture is poured onto ice water and the product is extracted with ethyl acetate (3×30 ml). The organic phases are dried (Na2SO4) and the solvent is distilled off in vacuo. The residue is purified by flash chromatography (7:3, toluene/ethyl acetate). 1-Ethyl-6-methyl-3-phenyl-1H-pyrimido[5,4-e][1,2,4]triazine-5,7-dione (44 mg, 28.8%) and 1-ethyl-4-oxy-3-phenyl-6-propyl-1H-pyrimido[5,4-e][1,2,4]triazine-5,7-dione (41 mg, 32%) are obtained.

1-Ethyl-6-methyl-3-phenyl-1H-pyrimido[5,4-e][1,2,4]triazine-5,7-dione
$^1$H-NMR: δ=7.75 (dd, 2 H, aryl), 7.6 (m, 3H, aryl), 4.4 (q, 2H, CH$_2$); 3.3 (3 H, NCH$_3$), 1.4 (t, 3H, CH$_3$)
MS (M+1) 284.2

1-Ethyl-6-methyl-4-oxy-3-phenyl-1H-pyrimido[5,4-e][1,2,4]triazine-5,7-dione
$^1$H-NMR: δ=8.2 (dd, 2H, aryl), 7.6 (m, 3H, aryl), 4.5 (q, 2H, CH$_2$); 3.3 (3 H, NCH$_3$), 1.5 (t, 3H, CH$_3$)
MS (M+1): 300.

EXAMPLES 3 AND 4

1-Ethyl-3,6-dimethyl-1H-pyrimido[5,4-e][1,2,4]triazine-5,7-dione (6) and 1-ethyl-3,6-dimethyl-4-oxy-1H-pyrimido[5,4-e][1,2,4]triazine-5,7-dione (7).

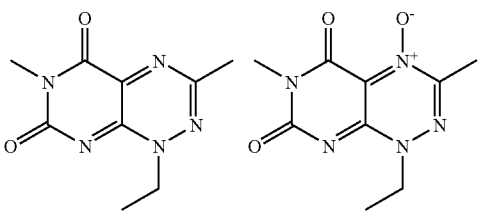

The compounds 6 and 7 are prepared, as described for 4 and 5, by reacting the hydrazine 3 (184 mg, 1 mmol) with acetaldehyde (57 µL, 1 mmol).

1-Ethyl-3,6-dimethyl-1H-pyrimido[5,4-e][1,2,4]triazine-5,7-dione (6)
Yield: 62 mg (28%)
$^1$H-NMR: δ=4.4 (q, 2H, NCH$_2$CH$_3$); 3.5 (s, 3H, CH$_3$), 3.4 (s, 3H, NCH$_3$); 1.45 (t, 3H, NCH$_2$CH$_3$).
MS (221.22): 222. (M+H)

1-Ethyl-3,6-dimethyl-4-oxy-1H-pyrimido[5,4-e][1,2,4]triazine-5,7-dione (7).
Yield: 21 mg (9%)
$^1$H-NMR: δ=4.57 (q, 2H, CH$_2$); 3.5 (s, 3H, CH$_3$), 1.5 (t, 3H, CH$_3$)
MS (237.22): 238.3. (M+H).

EXAMPLE 5

1-Ethyl-6-methyl-3-(4-propylphenyl)-1H-pyrimido[5,4-e][1,2,4]triazine-5,7-dione (8)

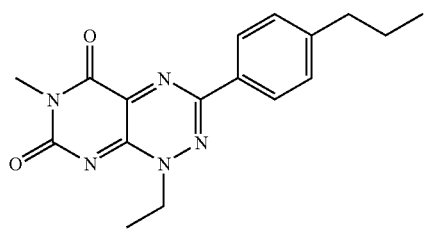

Compound 8 was obtained, as described for compounds 4 and 5, by reacting the hydrazine 3 (100 mg, 0.54 mmol) with 4-propylbenzylaldehyde (80 mg, 0.54 mmol) and purified by flash chromatography Yield: 43 mg (24.5%)
$^1$H-NMR: δ=8.15 (d, 2H, aryl), 7.4 (d, 2H, aryl), 4.5 (q, 2H, NCH$_2$CH$_3$); 3.35 (s, 3 H, NCH$_3$) 2.65 (t, 2H, benzyl, CH$_2$), 1.65 (m, 2H, CH$_2$CH$_2$CH$_3$), 1.45 (t, 3H, NCH$_2$CH$_3$), 0.95 (t, 3H, CH$_2$CH$_2$CH$_3$).
MS (325.37): 326.16 (M+H).

EXAMPLES 6 AND 7

1-Ethyl-6-methyl-3-phenyl-1H-pyrimido[5,4-e][1,2,4]triazine-5,7-dione (9) and 1-ethyl-6-methyl4-oxy-3-phenyl-1H-pyrimido[5,4-e][1,2,4]triazine-5,7-dione (10)

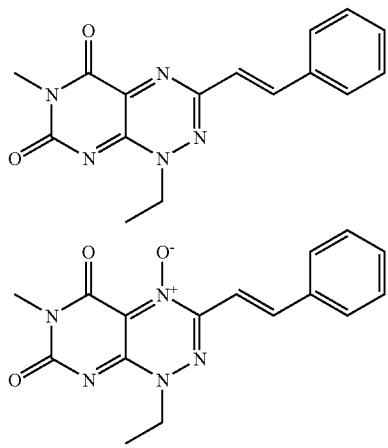

The compounds 9 and 10 were obtained, as described for compound 4 and 5, by reacting the hydrazine 3 (100 mg, 0.54 mmol) with cinnamaldehyde (71 mg, 0.54 mmol), and purified by flash chromatography.

1-Ethyl-6-methyl-3-phenyl-1H-pyrimido[5,4-e][1,2,4]triazine-5,7-dione (9)

Yield: 52 mg (31%)

$^1$H-NMR: δ=7.9 (m, 3H, 2 aryl-H, C$\underline{H}$=CH), 7.4 (m, 3H, aryl H); 7.3 (d, 1H C$\underline{H}$=CH), 4.4 (q, 2H, NC$\underline{H}_2$CH$_3$); 3.3 (s, 3H, NCH$_3$); 1.4 (t, 3H, NCH$_2$C$\underline{H}_3$).

MS (309.33): 310 (M+H)

Ethyl-6-methyl-4-oxy-3-phenyl-1H-pyrimido[5,4-e][1,2,4]triazine-5,7-dione (10)

Yield: 36 mg (20.5%)

$^1$H-NMR: δ=7.75 (m, 3H, 2 aryl-H, C$\underline{H}$=CH), 7.45 (m, 3H, 2 aryl H, C$\underline{H}$=CH), 4.4 (q, 2H, NC$\underline{H}_2$CH$_3$); 3.3 (s, 3H, NCH$_3$); 1.4 (t, 3H, NCH$_2$C$\underline{H}_3$).

MS (TOF MS ES+; 325.33): 325.

EXAMPLE 8

1-Ethyl-6-methyl-3-(3-phenoxyphenyl)-1H-pyrimido[5,4-e][1,2,4]triazine-5,7-dione (11)

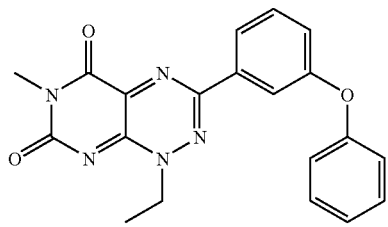

The compound 11 was obtained, as described for compound 4, by reacting the hydrazine 3 (100 mg, 0.54 mmol) with 3-phenoxybenzaldehdye (94 μl, 0.54 mmol), and purified by flash chromatography (2:1 toluene-EtOAc).

Yield: 88 mg (43%)

$^1$H-NMR: δ=8.05-7 (m, 9H, aryl-H); 4.5 (q, 2H, NC$\underline{H}_2$CH3); 3.3 (s, 3H, NCH$_3$); 1.45 (t, 3H, NCH$_2$C$\underline{H}_3$). MS (TOF MS ES+; 375.39): 375.

1-Propylbarbituric acid (12)

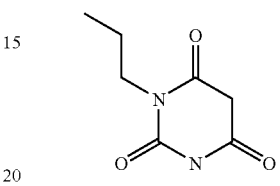

Metallic sodium (2.6 g, 113 mmol) is added to ethanol (60 ml). The mixture is stirred until the sodium has completely finished reacting. Diethyl malonate (116 ml, 105 mmol) and n-propylurea (10 g, 98 mmol) are then added and the mixture is stirred under reflux for 5 h. After conc. HCl (5 ml) and hot water (45 ml) have been added, the mixture is filtered and the filtrate is concentrated in vacuo. Ethanol is added to the residue and the mixture is stirred. The solid is filtered off with suction and dried.

Yield: 10.68 g (64%).

NMR: 726434 (32165-91)

6-Chloro-3-propyl-1H-pyrimidine-2,4-dione (13)

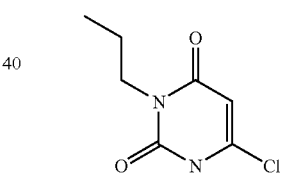

The compound 13 was obtained, as described for compound 1, by reacting the barbituric acid 12 (10 g, 58.8 mmol) with POCl3 (55 ml).

Yield: 2.6 g (23.5%)

6-(N-ethylhydrazino)-3-proeyl-1H-pyrimidine-2,4-dione (14)

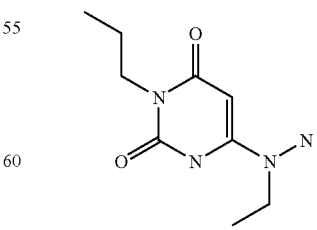

Compound 14 is obtained, as described in 3, by reacting compound 13 (1.5 g, 8 mmol) with ethylhydrazine (2 ml).

Yield: 528 mg (30.4%)

EXAMPLES 9 AND 10

1-Ethyl-6-propyl-3-phenyl-1H-pyrimido[5,4-e][1,2,4]triazine-5,7-dione (15) and 1-ethyl-6-propyl4-oxy-3-phenyl-1H-pyrimido[5,4-e][1,2,4]triazine-5,7-dione (16)

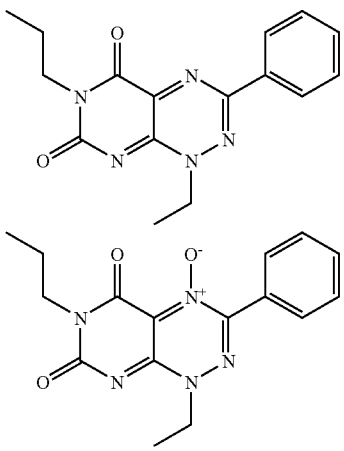

The compounds 15 and 16 are prepared, as described in 4 and 5, by reacting compound 14 (115 mg, 0.54 mmol) with benzaldehyde (55 µl, 0.54 mmol).

1-Ethyl-6-propyl-3-phenyl-1H-pyrimido[5,4-e][1,2,4]triazine-5,7-dione (15)

Yield: 44 mg (26%)

$^1$H-NMR: δ=8.2 (m, 2H, aryl-H), 7.6 (m, 3H, aryl-H); 4.5 (q, 2H, NC$\underline{H}_2$CH$_3$); 3.85 (q, 2H, NC$\underline{H}_2$CH$_2$CH$_3$); 1.6 (dq, 2H, NCH$_2$C$\underline{H}_2$CH$_3$); 1.5 (t, 3H, NCH$_2$C$\underline{H}_3$); 0.9 (t, 3 H, NCH$_2$CH$_2$C$\underline{H}_3$).

1-Ethyl-6-propyl-4-oxy-3-phenyl-1H-pyrimido[5,4-e][1,2,4]triazine-5,7-dione (16)

Yield: 41 mg (23.2%)

$^1$H-NMR: δ=8.0 (m, 2H, aryl-H), 7.6 (m, 3H, aryl-H); 4.4 (q, 2H, NC$\underline{H}_2$CH$_3$); 3.85 (q, 2H, NC$\underline{H}_2$CH$_2$CH$_3$); 1.58 (dq, 2H, NCH$_2$C$\underline{H}_2$CH$_3$); 1.4 (t, 3H, NCH$_2$C$\underline{H}_3$); 0.9 (t, 3H, NCH$_2$CH$_2$C$\underline{H}_3$).

1-Ethyl-6-propyl-3-[3,4-dimethoxyphenyl]-1H-pyrimido[5,4-e][1,2,4]triazine-5,7-dione (17)

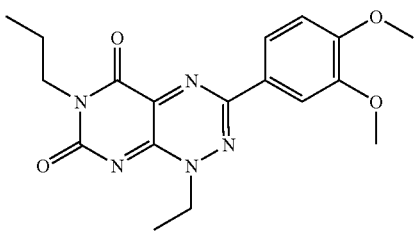

Compound 17 is prepared, as described in 4, by reacting the hydrazine 13 (115 mg, 0.54 mmol) with 3,4-dimethoxybenzaldehyde (90 mg, 0.54 mmol).

Yield: 31 mg (15.4%).

$^1$H-NMR: δ=7.85 (dd, 1H, aryl-H); 7.7 (d, 1H, aryl-H); 7, (dd, 1H, aryl-H); 4.5 (q, 2H, NC$\underline{H}_2$CH$_3$); 3.85 (m, 8H, 2×OC$\underline{H}_3$, NC$\underline{H}_2$CH$_2$CH$_3$); 1.6 (dt, 2H, NCH$_2$C$\underline{H}_2$CH$_3$); 1.45 (t, 3H, NCH$_2$C$\underline{H}_3$); 0.9 (t, 3H, NCH$_2$CH$_2$C$\underline{H}_3$).

1Ethyl-6-propyl-3-[3-phenoxyphenoxy]-1H-pyrimido[5,4-e][1,2,4]triazine-5,7-dione (18)

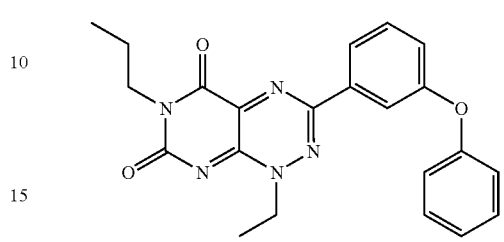

Compound 18 is prepared, as described for 4, by reacting the hydrazine 3 (115 mg, 0.54 mmol) with 3-phenoxybenzaldehyde (93 µl, 0.54 mmol).

Yield: 78 mg (35.8%)

$^1$H-NMR: δ=7.95 (dd, 1H, aryl-H); 7.8 (d, 1H, aryl-H); 7.63 (dd, 1H, aryl-H); 7.43 (m, 2H, aryl-H); 7.2 (m, 2H, aryl-H); 7.1 (m, 2H, aryl-H); 4.45 (q, 2H, NC$\underline{H}_2$CH$_3$); 3.85 (dt, 2H, NC$\underline{H}_2$CH$_2$CH$_3$); 1.6 (m, 2H, NCH$_2$C$\underline{H}_2$CH$_3$); 1.45 (t, 3H, NCH$_2$C$\underline{H}_3$); 0.9 (t, 3H, NCH$_2$CH$_2$C$\underline{H}_3$).

6-(N-Butylhydrazino)-3-methyl-1H-pyrimidine-2,4-dione (19)

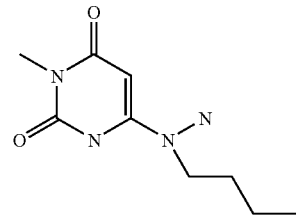

Compound 19 is prepared, as described in 3, by reacting chlorouracil 1 (1 g, 6.2 mmol) with butylhydrazine (5.3 g, 60 mmol).

Yield: 1.1 g (83%)

1-Butyl-6-methyl-3-[3-phenoxyphenyl]-1H-pyrimido[5,4-e][1,2,4]triazine-5,7-dione (20)

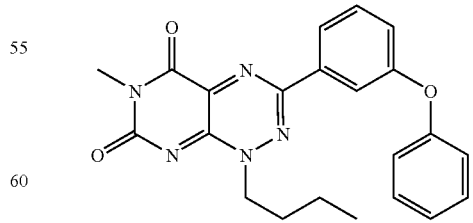

Compound 20 is prepared, as described for 4, by reacting the hydrazine 19 (176 mg, (0.54 mmol) with 3-phenoxybenzaldehyde (94 µl, 0.54 mmol).

Yield: 75 mg (34.5%)

$^1$H-NMR: δ=8.05 (m, 1H, aryl-H); 7.8 (d, 1H, aryl-H); 7.75 (dd, 1H, aryl-H); 7.43 (m, 2H, aryl-H); 7.15 (m, 2H, aryl-H); 7.1 (m, 2H, aryl-H); 3.9 (q, 2H, NC$\underline{H}_2$CH$_2$CH$_2$CH$_3$); 3.1 (s, 3H, NC$\underline{H}_3$); 1.6-1.3 (m, 4H, NCH$_2$C$\underline{H}_2$C$\underline{H}_2$CH$_3$); 0.9 (q, 2H, NCH$_2$CH$_2$H$_2$C$\underline{H}_3$);

1-Butyl-6-methyl-3-[3,4-dimethoxyphenyl]-1H-pyrimido[5,4-e][1,2,4]triazine-5,7-dione (21)

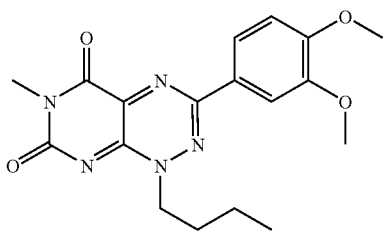

Compound 21 is prepared, as described in 4, by reacting the hydrazine 20 (176 mg, 0.54 mmol) with 3,4-dimethoxybenzaldehyde (88 mg, 0.54 mmol).

Yield: 24 mg (12%)

$^1$H-NMR: δ=7.95 (s, 1H, aryl-H); 7.6 (d, 1H, aryl-H); 7.45 (dd, 1H, aryl-H); 3.9-3.8 (m, 8H, 2×OCH$_3$, NC$\underline{H}_2$CH$_2$CH$_2$CH$_3$); 3.1 (s, 3H, NC$\underline{H}_3$); 1.6-1.2 (m, 4H, NCH$_2$C$\underline{H}_2$C$\underline{H}_2$CH$_3$); 0.9 (q, 2H, NCH$_2$CH$_2$CH$_2$C$\underline{H}_3$);

1-Butyl-6-metyl-3-phenyl-1H-pyrimido[5,4-e][1,2,4]triazine-5,7-dione (22)

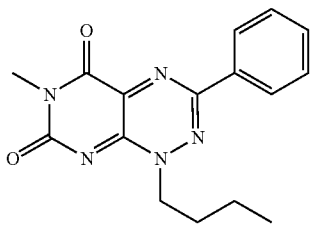

Compound 22 is prepared, as described in 4, by reacting the hydrazine 20 (176 mg, 0.54 mmol) with benzaldehyde (55 μl, 0.54 mmol).

Yield: 13 mg (7.8%)

We claim:

1. A method of lowering blood sugar which comprises administering to a patient in need thereof a therapeutically effective amount of a compound of a compound of formula I,

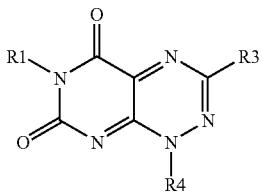

in which
R1 is (C$_1$-C$_6$)-alkyl;
R3 is (C$_1$-C$_6$)-alkyl-phenyl or (C$_2$-C$_6$)-alkenyl-phenyl, where the phenyl ring can be substituted by F, Cl, Br, OR13 or R13;
R4 is (C$_1$-C$_6$)-alkyl or (C$_1$-C$_6$)-alkylene-D; and
R13 is (C$_1$-C$_6$)-alkyl or phenyl;
or a pharmaceutically acceptable salt thereof.

2. A method of treating type 2 diabetes which comprises administering to a patient in need thereof a therapeutically effective amount of a compound of formula I,

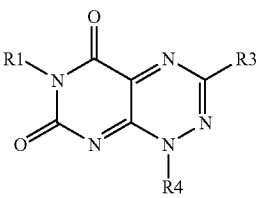

in which
R1 is (C$_1$-C$_6$)-alkyl;
R3 is (C$_1$-C$_6$)-alkyl-phenyl or (C$_2$-C$_6$)-alkenyl-phenyl, where the phenyl ring can be substituted by F, Cl, Br, OR13 or R13;
R4 is (C$_1$-C$_6$)-alkyl or (C$_1$-C$_6$)-alkylene-D; and
R13 is (C$_1$-C$_6$)-alkyl or phenyl;
or a pharmaceutically acceptable salt thereof.

3. A method of treating insulin resistance which comprises administering to a patient in need thereof a therapeutically effective amount of a compound of formula I,

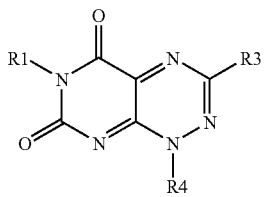

in which
R1 is (C$_1$-C$_6$)-alkyl;
R3 is (C$_1$-C$_6$)-alkyl-phenyl or (C$_2$-C$_6$)-alkenyl-phenyl, where the phenyl ring can be substituted by F, Cl, Br, OR13 or R13;
R4 is (C$_1$-C$_6$)-alkyl or (C$_1$-C$_6$)-alkylene-D; and
R13 is (C$_1$-C$_6$)-alkyl or phenyl;
or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,737,144 B2 |
| APPLICATION NO. | : 11/770106 |
| DATED | : June 15, 2010 |
| INVENTOR(S) | : Stefan Petry et al. |

It is certified that error appears in the above-identified patent and that said Letters Patent is hereby corrected as shown below:

Title Page;

On the first page, in field (54), in column 1, in "Title", line 1, delete "TRIAZINE-5-7-DIONES," and insert -- TRIAZINE-5,7-DIONES, --, therefor.

On the first page, in field (56), in column 2, under "Other Publications", line 2, delete "Gastic" and insert -- Gastric --, therefor.

On the first page, in field (56), in column 2, under "Other Publications", line 13, delete "(8-Demethytfervenulin)1," and insert -- "(8-Demethylfervenulin)1, --, therefor.

On page 2, in column 1, under "Other Publications", line 13, delete "5-Subsitituted" and insert -- 5-Substituted --, therefor.

On page 2, in column 2, under "Other Publications", line 10, delete "1-Demethylloxoflavins," and insert -- 1-Demethyltoxoflavins, --, therefor.

In column 1, line 1, delete "TRIAZINE-5-7-DIONES," and insert -- TRIAZINE-5,7-DIONES, --, therefor.

In column 2, line 8, delete "-($C_{1-4}$)-alkyl" and insert -- -($C_1$-$C_4$)-alkyl --, therefor.

In column 2, line 65, delete "ethylene-diamine." and insert -- ethylenediamine. --, therefor.

In column 5, line 61, delete "gluconeo-genesis" and insert -- gluconeogenesis --, therefor.

In column 7, line 8, delete "thiazolilinedione," and insert -- thiazolidinedione, --, therefor.

In column 7, line 52, delete "(4-chlor-2,5" and insert -- (4-chloro-2,5 --, therefor.

Signed and Sealed this
Twenty-first Day of June, 2011

David J. Kappos
*Director of the United States Patent and Trademark Office*

CERTIFICATE OF CORRECTION (continued)

U.S. Pat. No. 7,737,144 B2

In column 8, line 2, delete "Doprexin)," and insert -- Dopergin), --, therefor.

In column 11, line 28, delete "athero-sclerosis," and insert -- atherosclerosis, --, therefor.

In column 13, line 22, delete "X. J." and insert -- X. J., --, therefor.

In column 14, line 47, delete "($Na^2SO_4$)." and insert -- ($Na_2SO_4$). --, therefor.

In column 15, line 24, delete "pyrinido" and insert -- pyrimido --, therefor.

In column 15, line 25, delete "methyl4-oxy" and insert -- methyl-4-oxy --, therefor.

In column 15, line 52, delete "NaNO2" and insert -- $NaNO_2$ --, therefor.

In column 15, line 56, delete "Na2SO4" and insert -- $Na_2SO_4$ --, therefor.

In column 15, line 67, delete "(M+1)" and insert -- (M+1): --, therefor.

In column 16, line 61, delete "chromatography" and insert -- chromatography. --, therefor.

In column 17, line 2, delete "methyl4-oxy" and insert -- methyl-4-oxy --, therefor.

In column 17, line 41, delete "(M+H)" and insert -- (M+H). --, therefor.

In column 18, line 3, delete "3-phenoxybenzaldehdye" and insert -- 3-phenoxybenzaldehyde --, therefor.

In column 18, line 6-7, delete "(q, 2H, NC$\underline{H}_2$CH3);" and insert -- (q, 2H, NC$\underline{H}_2$CH$_3$); --, therefor.

In column 18, line 49, delete "POCl3" and insert -- $POCl_3$ --, therfeor.

In column 18, line 51, delete "3-proeyl" and insert -- 3-propyl --, therefor.

In column 19, line 2, delete "propyl4-oxy" and insert -- propyl-4-oxy --, therefor.

In column 20, line 4, delete "1Ethyl" and insert -- 1-Ethyl --, therefor.

In column 20, line 65, delete "(0.54" and insert -- 0.54 --, therefor.

In column 21, line 5, delete "NCH$_2$CH$_2$H$_2$C$\underline{H}_3$);" and insert -- NCH$_2$CH$_2$CH$_2$C$\underline{H}_3$). --, therefor.

In column 21, line 29, delete "NCH$_2$CH$_2$CH$_2$C$\underline{H}_3$);" and insert -- NCH$_2$CH$_2$CH$_2$C$\underline{H}_3$). --, therefor.

In column 21, line 31, delete "6-metyl" and insert -- 6-methyl --, therefor.

In column 21, line 53, in claim 1, delete "of a compound of a compound" and insert -- of a compound --, therefor.